United States Patent [19]

Klemmensen et al.

[11] 4,138,584
[45] Feb. 6, 1979

[54] PRODUCTION OF CHRYSANTHEMIC ACID ESTERS AND HOMOLOGUES THEREOF

[75] Inventors: Per D. Klemmensen, Lemvig; Hans Kolind-Andersen, Harboor; Hans B. Madsen, Lemvig, all of Denmark

[73] Assignee: A/S Cheminova, Lemvig, Denmark

[21] Appl. No.: 799,587

[22] Filed: May 23, 1977

[30] Foreign Application Priority Data

May 25, 1976 [GB] United Kingdom ............... 21630/76

[51] Int. Cl.² ............................................. C07C 67/30
[52] U.S. Cl. ................................. 560/124; 260/343.6
[58] Field of Search ...................... 260/343.6; 560/124

[56] References Cited

U.S. PATENT DOCUMENTS

| | | | |
|---|---|---|---|
| 3,077,496 | 2/1963 | Julia | 560/124 |
| 3,299,100 | 1/1967 | Phillips | 260/343.6 |
| 4,000,180 | 12/1976 | Punja | 560/124 |

OTHER PUBLICATIONS

Krapcho, Tetrahedron Letters, pp. 957–960 (1973).
Krapcho, Tetrahedran Letters, pp. 1091–94 (1974).

*Primary Examiner*—James O. Thomas, Jr.
*Assistant Examiner*—Michael Shippen
*Attorney, Agent, or Firm*—Watson, Cole, Grindle & Watson; Krapcho, Tetrahedran Letters, pp. 1091–1094 (1974).

[57] ABSTRACT

A three-step process for the production of chrysanthemic acid esters and their homologues of the formula:

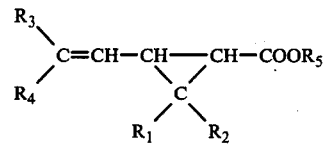

I in which
$R_1$ and $R_2$ are hydrogen or $C_1$–$C_6$ alkyl,
$R_3$ and $R_4$ are $C_1$–$C_6$ alkyl or halogen or, together with the C atom to which they are attached, form a cycloalkyl group, and
$R_5$ is $C_1$–$C_6$ alkyl, which comprises:
(1) decarboxylating a lactone of the formula:

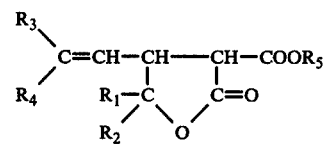

VIII (2) treating the resulting decarboxylated lactone to effect ring cleavage, halogenation and esterification to form an ester of the formula:

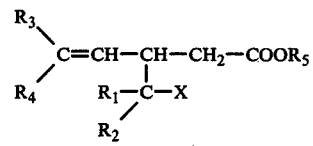

X in which X is Cl, Br or I, and
(3) treating the ester X with a base to effect internal condensation whereby the desired product of formula I is obtained.

The esters I are valuable intermediates for the preparation of synthetic pyrethroids having insecticidal activity.

5 Claims, No Drawings

PRODUCTION OF CHRYSANTHEMIC ACID ESTERS AND HOMOLOGUES THEREOF

BACKGROUND OF THE INVENTION

This invention is concerned with a process for the preparation of chrysanthemic acid esters and their homologues.

This invention is more specifically concerned with a process for the preparation of chrysanthemic acid esters and their homologues of the formula:

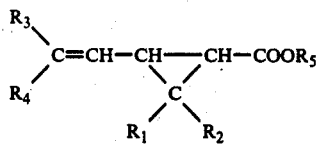

in which $R_1$ and $R_2$, which may be the same or different, are hydrogen or an alkyl group having 1 to 6 carbon atoms, preferably methyl;

$R_3$ and $R_4$, which may be the same or different, are an alkyl group having 1 to 6 carbon atoms, preferably methyl, or a halogen atom, preferably fluorine, chlorine or bromine, or, together with the carbon atom to which they are attached, form a cycloalkyl group; and $R_5$ is an alkyl group having 1 to 6 carbon atoms, preferably ethyl or propyl.

The compounds of formula I are valuable intermediates for the preparation of synthetic pyrethroids having insecticidal properties of the kind described for example in Nature, 246, 16th Nov. 1973, pages 169–170.

Processes for making some of the compounds of formula I and the corresponding acids ($R_5$ = H) are known.

Thus, chrysanthemic acid (I, $R_1 = R_2 = CH_3$, $R_3 = R_4 = CH_3$, $R_5 = H$) has been prepared by hydrolysis of pyrethrins of natural origin or by the synthesis of Staudinger et al, *Helv. Chim. Acta* (1924) 7, p 390, further developed by Campbell et al, *J. Chem. Soc.*, (1945), p 283. This synthesis, which starts with the reaction of ethyl diazoacetate with 2,5-dimethyl-hexa-2,4-diene and leads to a mixture of the (dl)-cis- and (dl)-trans-chrysanthemic acids, is, however, rather difficult to carry out because of the instability of ethyl diazoacetate. This instability makes the industrial use of this process very difficult. A similar synthesis, in which ethyl diazoacetate is replaced by diazoaceto-nitrile, gives pure (dl)-trans-chrysanthemic acid, but involves even greater risks.

U.S. Pat. No. 3,077,496 describes a process for the preparation of (dl)-trans-chrysanthemic acid in which 4-methyl-3-isobutenyl-γ-valerolactone is converted into alkyl 5-methyl-3-(1-halogeno-isopropyl)-hex-4-enoate, followed by cyclisation of this ester into a crysanthemic acid ester, and saponification.

U.S. Pat. No. 3,354,196 describes converting intermediates of the formula

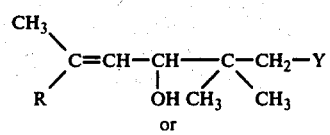

or

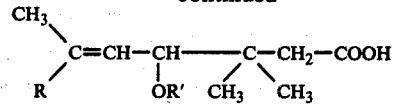

in which R is hydrogen or methyl, Y is —CN or —COOR', and R' is a lower alkyl radical, into intermediates of the formula

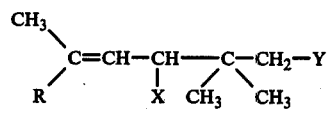

in which X is a reactive ester residue, such as a halogen atom or a sulphonic ester residue, or an aliphatic or aromatic carboxylic ester residue, and then converting the intermediates IV to compounds of the formula:

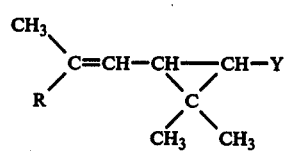

which are, in turn, converted to chrysanthemic acid or its lower homologue (in which R = H) by saponification.

U.S. Pat. No. 3,652,652 describes a process using 4-methyl-3-(2-methallyl)-γ-valerolactone as the starting compound; this compound is reacted with any halogenating agent capable of effecting ring cleavage to form a γ-halogeno-acyl halide. The compound obtained is reacted with an alkanol. Depending on the reaction conditions, that is upon whether or not any hydrogen halide is evolved during the initial halogenation step and upon whether or not a hydrogen halide is present with the alkanol in the second step, one or both of the following compounds VI and VII are obtained:

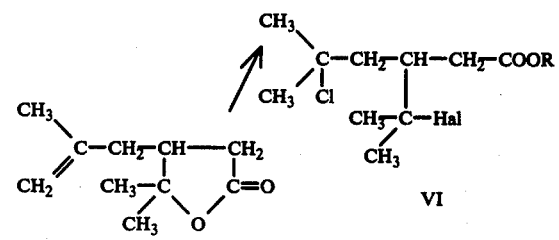

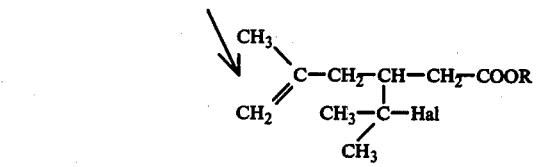

where Hal is a halogen atom and R is an alkyl radical.

By cyclising under suitable conditions, the intermediate VI can be directly converted into a chrysanthemic acid ester. The intermediate VII can be cyclised to form the cyclopropane ring and the product then isomerised by heating in the presence of toluene-p-sulphonic acid or other organic sulphonic acid to shift the double bond and thus obtain a chrysanthemic acid ester.

SUMMARY OF THE INVENTION

We have now developed an improved process for preparing chrysanthemic acid esters and homologues and analogues thereof of formula I; in comparison with the known processes described above, our new process provides significant improvements in starting material and process economy.

The process according to the invention comprises (1) heating a lactone of the formula:

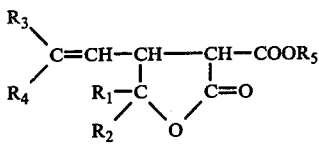

VIII in which $R_1$, $R_2$, $R_3$, $R_4$ and $R_5$ have the above-stated meanings, to an elevated temperature in the presence of an inert solvent in order to effect decarboxylation and obtain a lactone of the formula:

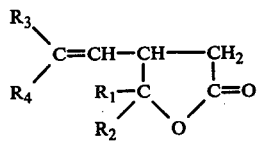

IX (2) reacting the lactone IX with a halogenating or hydrohalogenating agent and with an aliphatic alcohol $R_5OH$, where $R_5$ has the above-stated meaning, to effect ring cleavage, halogenation and esterification to obtain an ester of the formula:

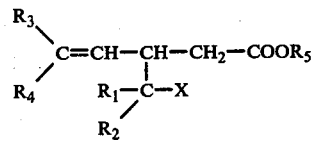

X in which X is chlorine, bromine or iodine, preferably chlorine, and (3) treating the ester X with a base to effect dehydrohalogenation and internal condensation whereby the desired product of formula I is obtained.

Steps (1) to (3) of the process according to the invention and the preferred conditions for use therein, will now be described in greater detail.

Step (1), decarboxylation of a lactone of formula VIII, is carried out at elevated temperature, preferably 100° to 200° C., and in the presence of an inert solvent. Any protic or aprotic solvent may be used. Preferred solvents are dimethyl sulphoxide (DMSO), dimethyl formamide (DMF), hexamethylphosphoric triamide (HMPA), N-methyl-2-pyrolidone (NMP), methanol, water and mixtures of two or more of these solvents; mixtures of methanol and water are particularly preferred. The reaction may be carried out with or without a catalyst, such as an alkali metal or quaternary ammonium halide, preferably sodium bromide, potassium chloride or tetraethylammonium bromide. It is, in general, preferred not use to a catalyst in step (1).

Step (2) is preferably carried out at an elevated temperature, preferably 50° to 150° C., but in the presence of a catalyst. Suitable catalysts are Lewis acids, for example $FeCl_3$, $NiCl_2$, $BF_3$ and $ZnCl_2$, of which $FeCl_3$ is preferred. Suitable halogenating or hydrohalogenating agents are, for example, $SOCl_2$, HCl, $PCl_3$, $PCl_5$, $POCl_3$, $COCl_2$ and $CSCl_2$.

The steps of (i) ring cleavage and halogenation and (ii) esterification may be carried out simultaneously, that is in a single reaction mixture (which contains the lactone IX, the halogenating or hydrohalogenating agent, the alcohol $R_5OH$ and, preferably, the catalyst) or sequentially, that is the lactone IX is first reacted with the halogenating or hydrohalogenating agent, preferably in the presence of the catalyst, and then with the alcohol $R_5OH$. In the latter case, that is with sequential operation, it is preferred not to isolate the intermediate, but to add the alcohol $R_5OH$ to the reaction mixture when ring cleavage and halogenation is complete.

It is preferred to carry out steps (i) and (ii) above simultaneously using a reaction mixture comprising $SOCl_2$ as the halogenating agent, ethyl or propyl alcohol as the alcohol $R_5OH$, and $FeCl_3$ as the catalyst. It is further preferred to carry out these reactions under superatmospheric pressure; suitable pressures will depend upon the equipment used, but may, for example, be up to 20 atmospheres or more.

Step (3) is preferably carried out at low temperature, preferably not more than 0° C., in the presence of an inert solvent. The choice of solvent is not critical and any polar or non-polar, protic or aprotic solvent may be used. Preferred solvents are t-butanol, dimethyl formamide, and ethers, such as dioxan, tetrahydrofuran or dimethoxyethane. Any suitable inorganic or organic base may be used, preferred bases being sodium or potassium ethoxide, tert.-butoxide and tert.-amyloxide.

The starting compounds used in the process according to the invention, the lactones of formula VIII, can be obtained, for example, as described in our copending U.S. Application Ser. No. 756,906.

In order that the invention may be more fully understood, the following examples are given by way of illustration only:

EXAMPLE 1

(1) A solution of 50 g (0.18 mole) of 3-carbethoxy-4-(2,2-dichlorovinyl)-5,5-dimethyl-γ-butyrolactone and 17 g of sodium bromide in 270 ml of wet dimethylsulphoxide was stirred for 3 hours at 130° C. After cooling the reaction mixture, water and ethyl ether were added and stirring was continued for half an hour. The ether layer was separated and evaporated to give 4-(2,2-dichlorovinyl)-5,5-dimethyl-γ-butyrolactone in a yield of 95%. M.p. 115°–117° C.

(2) 1.83 g (0.009 mole) of 4-(2,2-dichlorovinyl)-5,5-dimethyl-γ-butyrolactone and 4.28 g (0.036 mole) of $SOCl_2$ were mixed with 100 ml of HCl-saturated benzene and the mixture was heated for 3 hours. An excess of HCl-saturated $C_2H_5OH$ was then added and the mixture was refluxed for a further 3 hours. Ethyl 3-(2,2-dichlorovinyl)-4-chloro-4-methyl-pentanoate was isolated from the reaction mixture in a yield of 60%.

(3) 1.37 g (0.005 mole) of ethyl 3-(2,2-dichlorovinyl)-4-chloro-4-methyl-pentanoate and 3.4 g (0.03 mole) of potassium tert. - butoxide were reacted in 150 ml of dry toluene under a nitrogen atmosphere. The reaction was carried out at temperatures from −70° to −10° C. and gave a nearly quantitative mixture of cis and trans ethyl 2,2-dimethyl-3-(2,2-dichlorovinyl)-cyclopropane-carboxylate.

EXAMPLE 2

(1) A solution of 50 g (0.18 mole) of 3-carbethoxy-4-(2,2-dichlorovinyl)-5,5-dimethyl-γ-butyrolactone and 1.7 g of sodium bromide in 270 ml of wet dimethylsulphoxide was stirred for 3 hours at 130° C. After cooling the reaction mixture, water and ethyl ether were added and stirring was continued for half an hour. The ether layer was separated and evaporated to give 4-(2,2-dichlorovinyl)-5,5-dimethyl-γ-butyrolactone in a yield of 95%. M.p. 115°-117° C.

(2) 1.83 g (0.009 mole) of 4-(2,2-dichlorovinyl)-5,5-dimethyl-γ-butyrolactone and 4.28 g (0.036 mole) of $SOCl_2$ were mixed with 100 ml of HCl-saturated benzene and 0.5 g of $FeCl_3$, the mixture was then heated for 15 minutes. An excess of HCl-saturated $C_2H_5OH$ was then added and the mixture was refluxed for a further 3 hours. Ethyl 3-(2,2-dichlorovinyl)-4-chloro-4-methyl-pentanoate was isolated from the reaction mixture in a yield of 60%. B.p. 100°-5° C./0.2-0.3 mm Hg.

(3) A solution of 274 g (1 mole) ethyl 3-(2,2-dichlorovinyl)-4-chloro-4-methyl-pentanoate in 1.5 liter of dry dimethylformamide (DMF) was cooled to 0° C. A suspension of 101 g (1.05 mole) sodium t-butoxide in 1 liter dry DMF was added to the solution over a period of 2 hours. The reaction mixture was then neutralized with dry HCl. The DMF was distilled off under vacuum to give a 90% yield of ethyl 2,2-dimethyl-3-(2,2-dichlorovinyl)-cyclopropane carboxylate. B.p. 85°-95° C./0.2-0.3 mm Hg.

EXAMPLE 3

(1) A solution of 267 g (1 mole) of 3-carbethoxy-4-(2,2-dichlorovinyl)-5,5-dimethyl-γ-butyrolactone in 750 ml $CH_3OH$ and 250 ml $H_2O$ was heated in an autoclave and held for 4 hours at 140° C. After completion of the reaction, the water and methanol were distilled off. 4-(2,2-Dichlorovinyl)-5,5-dimethyl-γ-butyrolactone was obtained in nearly quantitative yield, m.p. 115° C.

(2) A 2 l. autoclave was charged with 418 g (2 mole) of 4-(2,2-dichlorovinyl)-5,5-dimethyl-γ-butyrolactone, 10 g $FeCl_3$, and 952 g (8 mole) thionyl chloride. 368 g (8 mole) of ethanol was pumped into the autoclave and the pressure rose to 12-14 atm. The autoclave was then heated to 85° C. and the reaction proceeded for 1 hour. The pressure rose to 20 atm. and was kept at this level by releasing HCl. After cooling and releasing the HCl pressure, ethyl 2-carbethoxy-3-(2,2-dichlorovinyl)-4-methyl-4-chloro-1-pentanoate was obtained in 80% yield; b.p. 100°-105° C./0.2-0.3 mm Hg.

(3) The product of step (2) was treated as described in Example 2(3) to give ethyl 2,2-dimethyl-3-(2,2-dichlorovinyl)-cyclopropane-carboxylate in a 90% yield.

EXAMPLE 4

(1) A solution of 267 g (1 mole) of 3-carbethoxy-4-(2,2-dichlorovinyl)-5,5-dimethyl-γ-butyrolactone in 600 ml dimethyl formamide (DMF) and 27 ml (1.5 mole) of water, was heated to reflux for 4-6 hours. After completion of the reaction, DMF was distilled off under a pressure of 10-50 mm Hg to give a 90% yield of 4-(2,2-dichlorovinyl)-5,5-dimethyl-γ-butyrolactone, m.p. 114° C.

(2) and (3). The product of step (1) was subjected to steps (2) and (3) as described in Example 3(2) and Example 1(3) respectively to give ethyl 2,2-dimethyl-3-(2,2-dichlorovinyl)-cyclopropane-carboxylate.

What is claimed is:

1. A process for the preparation of chrysanthemic acid esters and their homologues of the formula:

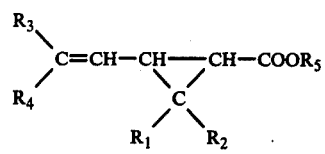

wherein
$R_1$ and $R_2$ are individually selected from the group consisting of hydrogen and alkyl groups having 1 to 6 carbon atoms,
$R_3$ is a halogen atom;
$R_4$ is a halogen atom; and
$R_5$ is an alkyl group having 1 to 6 carbon atoms,
which comprises the steps of:
(1) heating a lactone of the formula:

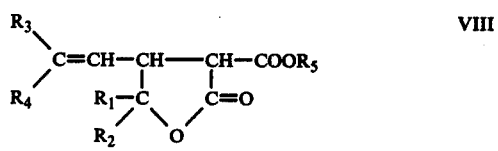

in which $R_1$, $R_2$, $R_3$, $R_4$ and $R_5$ have the above stated meanings, to a temperature of from about 100° C. to about 200° C. in the presence of water and an inert solvent to effect decarboxylation and to obtain a lactone of the formula:

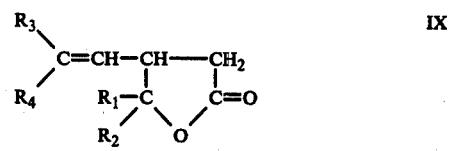

(2) reacting the lactone IX with thionyl chloride and with an aliphatic alcohol $R_5OH$, wherein $R_5$ has the above-stated meaning, at a superatmospheric pressure to bring about, in the same reaction mixture, ring cleavage, halogenation and esterification without isolating any intermediate product, whereby there is obtained an ester of the formula:

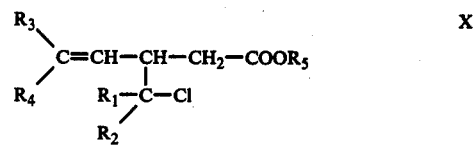

(3) treating the ester X with a base to effect dehydrohalogenation and internal condensation whereby the desired compound of formula I is obtained.

2. A process as set forth in claim 1, wherein the inert solvent used in step (1) is selected from the group consisting of dimethyl sulphoxide, dimethyl formamide, hexamethylphosphoric triamide, N-methyl-2-pyrrolidone and methanol and mixtures of at least two thereof.

3. A process as set forth in claim 1, wherein step (2) is carried out in the absence of a catalyst.

4. A process as set forth in claim 1, wherein step (2) is carried out in the presence of a Lewis acid as catalyst.

5. A process as set forth in claim 4, wherein the catalyst is $FeCl_3$.